United States Patent [19]

Rand

[11] Patent Number: 5,183,919
[45] Date of Patent: Feb. 2, 1993

[54] PROCESS FOR THE PREPARATION OF DIARYL CARBONATES

[75] Inventor: Cynthia L. Rand, Sanford, Mich.

[73] Assignee: The Dow Chemical Company, Midland, Mich.

[21] Appl. No.: 739,778

[22] Filed: Jul. 30, 1991

Related U.S. Application Data

[63] Continuation of Ser. No. 451,893, Dec. 18, 1989, abandoned.

[51] Int. Cl.⁵ ............................................. C07C 69/96
[52] U.S. Cl. ..................................................... 558/274
[58] Field of Search ........................................ 558/274

[56] References Cited

U.S. PATENT DOCUMENTS

| | | | |
|---|---|---|---|
| 2,362,865 | 7/1941 | Tryon et al. | 558/274 |
| 3,170,946 | 2/1965 | Kilsheimer et al. | 558/282 |
| 3,211,774 | 10/1965 | Stephens | 558/281 |
| 3,211,776 | 10/1965 | Stephens | 558/281 |
| 3,234,261 | 2/1966 | Kurkjy et al. | 558/274 |
| 3,234,263 | 2/1966 | Kurkjy et al. | 558/274 |
| 3,251,873 | 5/1966 | Kurkjy et al. | 558/274 |
| 3,275,674 | 9/1966 | Bottenbruch et al. | 558/268 |
| 4,012,406 | 3/1977 | Büysch et al. | 558/274 |
| 4,366,102 | 12/1982 | Rauchaschwalbe et al. | 558/274 |

FOREIGN PATENT DOCUMENTS 1361228  6/1963  France.

*Primary Examiner*—Jose G. Dees
*Assistant Examiner*—Joseph Conrad, III

[57] ABSTRACT

A process and a catalyst for the homogeneous liquid phase reaction of aromatic haloformates with aromatic hydroxy compounds for the production of diaryl carbonates with the elimination of anhydrous hydrogen halide. The catalysts of the present invention comprise at least one aromatic heterocyclic nitrogen compound. These catalysts permit the production of the products in very high yield, and the reaction proceeds at high rates.

18 Claims, No Drawings

PROCESS FOR THE PREPARATION OF DIARYL CARBONATES

CROSS-REFERENCE TO RELATED APPLICATION

This is a continuation of application Ser. No. 07/451,893, filed Dec. 18, 1989, now abandoned.

BACKGROUND OF THE INVENTION

1. Field of the Invention

The present invention relates to a process and a catalyst for the production of diaryl carbonates, and more particularly to a process and a homogeneous catalyst for the homogeneous liquid phase reaction of aromatic haloformates with aromatic hydroxy compounds for the production of diaryl carbonates with the elimination of anhydrous hydrogen halide.

2. Description of the Related Art

Prior art methods for the production of diaryl carbonates have used the interfacial route involving a two phase reaction system, and various homogeneous catalytic systems. The interfacial route involves the neutralization of the aromatic hydroxy compound with caustic and the subsequent reaction of an aqueous solution of the phenate type salt of the aromatic hydroxy compound with a carbonyl halide, usually phosgene. In the case where the desired product is diphenyl carbonate, excess caustic to insure the complete neutralization of phenol results in a loss of about 20 percent of the phosgene. Salt which represents the loss of two chlor/alkali equivalents is produced. As a consequence, the aqueous stream coming from this reaction process requires treatment prior to disposal. Caustic equivalents include the Group 1, 2, 11 and 12 hydroxides, oxides, carbonates and phosphates.

The prior art alternatives to the above described interfacial route to diaryl carbonates are various homogeneous catalytic processes. U.S. Pat. No. 2,362,865 discloses the use of metal phenates as catalysts in the reaction of phenol and phosgene to form diphenyl carbonate in a process in which the phenol is in the liquid phase. U.S. Pat. Nos. 3,234,261 and 3,234,263 relate to the formation of diaryl carbonates from various chloroformates by reaction with metal oxides, with the process of the '263 patent employing a tertiary amine base as a catalyst. Related processes are disclosed in French Patent No. 1,361,228 and U.S. Pat. No. 3,251,873. U.S. Pat. No. 4,366,102 discloses a process which employs various organic phosphorous compounds as catalysts for the reaction of a phenol and phosgene to form an aromatic chloroformic ester.

A process for the reaction of aromatic hydroxy compounds with carbonyl halides to produce diaryl carbonates which employs a heterogeneous catalyst system is described in U.S. patent application Ser. No. 429,954 filed on Oct. 26, 1989, by Harley et al.

The use of organophosphines as catalysts for the reaction of an aromatic haloformate with an aromatic hydroxy compound which is carried out in an inert reaction medium is describe in U.S. patent application Ser. No. 451,894, filed of even date herewith, by Rand.

U.S. Pat. No. 3,170,946 discloses a process for the preparation of arylchloroformates using aromatic amine catalysts, and U.S. Pat. Nos. 3,211,774, 3,211,776 and 3,275,674 disclose processes for the preparation of aromatic esters of chloroformic acid using aromatic amine catalysts. U.S. Pat. No. 4,012,406 discloses a process for the preparation of diaryl carbonates by the reaction of aromatic monohydroxy compounds with phosgene with the aid of an aromatic heterocyclic basic nitrogen compound as a catalyst. Many such catalysts are effective for the conversion of haloformates and aromatic hydroxy compounds into diaryl carbonates, as would be expected, since a haloformate is an intermediate in the reaction of an aromatic hydroxy compound and phosgene to form the same product. The '406 patent teaches that the catalyst may be any basic nitrogen compound in which the nitrogen is contained in an aromatic 5- or 6-membered ring and which does not have any other functional groups (e.g. —$NH_2$ or —OH groups) which are liable to form firm bonds with phosgene or carbonates under reaction conditions.

SUMMARY OF THE INVENTION

The diaryl carbonates produced by the present invention may be converted into polycarbonate resins for use as molding resins by application of heat or some other suitable technique.

The general objective of the present invention is to avoid the disadvantages of the prior art methods of production of diaryl carbonates. These include the water and salt disposal problem associated with the interfacial method, and catalyst degradation and regeneration problems associated with various homogeneous catalytic systems. Another objective of the present invention is to employ homogeneous organic catalyst systems with their numerous technical advantages. Surprisingly, contrary to the teachings of the prior art, it has been found that aromatic heterocyclic nitrogen compounds which are activated by reactive substituents promote the reaction between aromatic hydroxy compounds and aromatic haloformates to form diaryl carbonates in very high yields. The rates observed in the process of the present invention are much faster than those observed for prior art processes employing as catalysts heterocyclic nitrogen bases which are unsubstituted or substituted with non-reactive groups.

The process of the present invention for the production of aromatic carbonates comprises contacting an aromatic haloformate with an aromatic hydroxy compound in the presence of a catalytic amount of a catalyst which comprises at least one aromatic heterocyclic nitrogen compound which has been activated by at least one reactive substituent. The process is carried out in an inert reaction medium comprising an inert atmosphere, and, optionally, a noninteracting solvent.

DESCRIPTION OF THE PREFERRED EMBODIMENTS

Desirable aromatic hydroxy starting materials are represented by the general formula

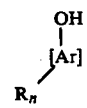

where Ar is an aryl or substituted aryl group with one or more fused rings, R independently selected each occurrence is alkyl, aryl, alkenyl, aryloxy, or alkoxy of 1–12 carbon atoms, and n is an integer. A preferred aromatic hydroxy starting material is represented by the formula

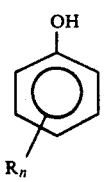

where R independently selected each occurrence is alkyl, aryl, alkenyl, aryloxy, or alkoxy of 1–12 carbon atoms, and n is an integer of 0–5. More highly preferred are phenols wherein R independently selected each occurrence is alkyl, aryl, alkenyl, aryloxy, or alkoxy of 1–6 carbon atoms and n is an integer of 0–3. Other desirable aromatic hydroxy starting materials are bisphenols and naphthols. Highly preferred aromatic hydroxy starting materials are phenol and Bisphenols A and F.

Suitable aryl haloformates of the formula $R_n$—[Ar]—O—C(O)—X include those in which $R_n$—[Ar]—O— is selected from the same group as $R_n$—[Ar]—O— of the aromatic monohydroxy compound, as discussed above. The $R_n$—[Ar]—O— group of the haloformate may be the same or different from that of the monohydroxy compound. X is a halogen, and a preferred halogen is chlorine.

In a preferred embodiment the aromatic monohydroxy compound is phenol, the aromatic haloformate is phenyl chloroformate and the products of the reaction are diphenyl carbonate (DPC) and anhydrous hydrogen chloride.

Catalysts for the process of the present invention comprise at least one aromatic heterocyclic nitrogen compound which has been activated by at least one reactive substituent. A preferred reactive substituent is —OH. Any non-reactive substituent can be placed on the ring in any position and in any combination so long as there is at least one reactive substituent in one activating position. Examples include 2-hydroxypyridine, 3-hydroxypyridine, 4-hydroxypyridine, 2-hydroxy-4-methylpyridine, 2-hydroxy-4-methoxypyridine and 4-chloro-2-hydroxy-pyridine. In addition to nitrogen the ring may also contain other heteroatoms such as oxygen, sulfur or additional nitrogen atoms. Examples include 2-hydroxy-4-methylpyrimidine and 2-hydroxypyrimidine. Additional aromatic rings may be fused to the basic structure of the catalyst as well, with examples including 8-hydroxyquinazoline and 2-hydroxyquinoline.

A catalytic amount of the catalyst may be dissolved, dispersed or supported in the reaction medium. In one embodiment of the present invention the catalyst is simply dispersed in the reaction medium. If the reaction medium includes a noninteracting solvent it is desirable that the catalyst dissolve in the solvent.

The concentration of catalyst which provides a catalytic amount of the catalyst in the reaction system of the process of the present invention can range from about 0.1 percent to about 10 percent on a mole percent basis based on the reactants. A preferred range for the concentration of the catalyst is from about 0.5 mole percent to about 5 mole percent, with the most preferred range being from about 2 mole percent to about 4 mole percent.

Under the reaction conditions used in the process of the present invention the catalyst of the present invention to some extent is converted from the free base form into the hydrohalide. Since the position of the equilibrium depends upon the equilibrium constant for the dissociation equilibrium and other factors, such as temperature and solvent, various relative amounts of free base and salt forms of the catalyst may be present. If the base is introduced to the system as the hydrohalide, it will dissociate to yield the same balance as would prevail after some reaction has taken place when introduced as the free base.

The process of the present invention desirably is carried out in an inert reaction medium which comprises an inert atmosphere, preferably nitrogen. The reaction may be run with or without a noninteracting solvent. In one embodiment solvents are used which dissolve the catalyst. Suitable solvents include aromatic hydrocarbons, which may be halogenated, of from 6 to 16 carbon atoms. Examples of desirable solvents include xylene, toluene, ethyleenzene, cumene, diisopropylbenze, chlorobenzene and dichlorobenzene. Other desirable solvents include aliphatic halogenated hydrocarbons such as trichloroethylene, methylene chloride and tetrachloroethylene. A preferred solvent is 1,2-dichlorobenzene (ODCB). A mixture of two or more solvents may be used.

In another embodiment the aromatic haloformate serves as the reaction medium as well as being a reactant.

The process of the present invention may be carried out at temperatures up to the temperature at which the catalyst becomes unstable and decomposes. The desired temperature range is from about 80° C. to about 250° C., with the preferred temperature range being from about 150° C. to about 200° C.

The mole ratio of the reactants can vary. However, a preferred ratio of aromatic haloformate to aromatic hydroxy compound is from about 0.9:1 to about 1:1.5.

The hydrogen chloride produced in the reaction can be removed continuously or intermittently, as desired, and as necessary to relieve the pressure build-up due to the production of this gaseous product.

The following examples and comparative examples are provided to illustrate the process of the present invention, and are not intended to limit the scope of the present invention in any way.

EXAMPLE 1

A series of experiments were run under a standard set of conditions which utilizes the following ratio of solvent, reactants and catalyst: 1,2-dichlorobenzene (15 mL), phenol (22 mmol), phenyl chloroformate (11 mmol) and three mol percent of catalyst based on the total number of phenyl groups (33 mmol). The phenol and phenyl chloroformate are weighed into a vial, diluted with 15 mL of 1,2-dichlorobenzene (ODCB) and added through a septum to a five necked 25 mL round bottomed flask which has been purged with nitrogen. When the reaction temperature is constant at 150°–152° C., the catalyst, dissolved in 3 mL of ODCB, is added to the hot solution. The extent of reaction is measured by titration of the evolved HCl, since, from the stoichiometry of the reaction, the amount of HCl evolved over time is equal to the amount of diphenyl carbonate (DPC) which is formed. Corrections for salt formation between the catalyst and an equivalent of HCl are included when appropriate. The final yields of DPC are verified by liquid chromatography (LC) analysis.

In the above manner phenyl chloroformate(1.877 g) and phenol (2.1053 g) were allowed to react in the presence of 2-hydroxypyridine (0.0954 g). Rapid evolution of HCl was immediately evident. After about 10 minutes the yield was approximately 70%. Within experimental limitations, at 40 minutes the reaction essentially went to completion as analyzed by both titration (95% yield of DPC) and LC analysis versus an internal standard (99% yield of DPC). LC analysis also clearly demonstrated that the catalyst was unchanged and present in the amount originally added.

In comparison, under comparable experimental conditions, when catalyzed with pyridine the reaction rate was much slower and a lower yield was obtained. Experiments utilizing 2-chloropyridine, 2-mercaptopyridine and 3,5,6-trilchloro-2-pyridinol as the catalyst showed that the catalytic activity of these compounds is inferior even to pyridine. 4-N,N-dimethylaminopyridine, which is a known catalyst for the reaction of acid chlorides and chloroformates with nucleophiles such as phenol, also showed inferior catalytic activity.

What is claimed is:

1. A process for the production of a diaryl carbonate comprising contacting an aryl haloformate with a phenolic compound in the presence of a catalytic amount of a catalyst comprising at least one aromatic heterocyclic nitrogen compound which has been activated by at least one hydroxyl substituent.

2. The process of claim 1 wherein the aryl haloformate is phenyl chloroformate.

3. The process of claim 1 wherein the phenolic compound is represented by the formula:
where R independently each occurrence is selected from the group consisting of alkyl, aryl, alkenyl, aryloxy, or alkoxy of 1-12 carbon atoms and n is an integer of 0-5.

4. The process of claim 3, wherein R independently selected each occurrence is alkyl, aryl, alkenyl, aryloxy, or alkoxy or 1-6 carbon atoms and n is an integer of 0-3.

5. The process of claim 1 wherein the aromatic hydroxy compound is phenol, a cresol, an alkyl phenol, an alkoxy phenol, a halogenated phenol, Bisphonel A, Bisphenol F or naphthol.

6. The process of claim 1 wherein the aromatic heterocylcic nitrogen compound of the catalyst is 2-hydroxypyridine, 3-hydroxypyridine, 4-hydroxypyridine, 2-hydroxy-4-methylpyridine, 2-hydroxy-4-methoxypyridine or 4-chloro-2-hydroxypyridine.

7. The process of claim 1 wherein the heterocyclic nitrogen compound of the catalyst is 2-hydroxy-4-methylpyrimidine, 2-hydroxypyrimidine, 8-hydroxyquinazoline or 2-hydroxyquinoline.

8. The process of claim 1 wherein the concentration of the catalyst is from about 0.1 percent to about 10 percent on a mole percent basis based on the number of moles of the reactants.

9. The process of claim 8 wherein the concentration of the catalyst is from about 0.5 mole percent to about 5 mole percent.

10. The process of claim 9 wherein the concentration of the catalyst is from about 2 mole percent to about 4 mole percent.

11. The process of claim 1 wherein the process is carried out in an inert atmosphere.

12. The process of claim 1 conducted in the presence of a noninteracting solvent.

13. The process of claim 12 wherein the noninteracting solvent comprises xylene, cumene, toluene, ethylbenzene, diisopropylbenzene, chlorobenzene, dichlorobenzene, trichloroethylene, methylene chloride, tetrachloroethylene, or a mixture of two or more thereof.

14. The process of claim 13 wherein the noninteracting solvent comprises 1,2-dichlorobenzene.

15. The process of claim 1 wherein said process is carried out at a temperature from about 80° C. to about 250° C.

16. The process of claim 15 wherein said process is carried out at a temperature from about 150° C. to about 200° C.

17. The process of claim 1 wherein the mole ratio of aryl haloformate to the phenolic compound is from about 0.9:1 to about 1:1.5.

18. The process of claim 1 wherein the aryl haloformate is the reaction medium for the process.

* * * * *

UNITED STATES PATENT AND TRADEMARK OFFICE
CERTIFICATE OF CORRECTION

PATENT NO.  :  5,183,919
DATED       :  February 2, 1993
INVENTOR(S) :  Cynthia L. Rand It is certified that error appears in the above-identified patent and that said Letters Patent is hereby corrected as shown below:

Column 5, line 30, following "formula:", insert the following formula:

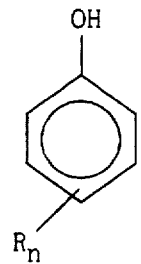

Column 6, line 6, following "wherein the" insert --aromatic--.

Signed and Sealed this

Eleventh Day of January, 1994

Attest:

BRUCE LEHMAN

Attesting Officer      Commissioner of Patents and Trademarks